United States Patent
Ferrari

(10) Patent No.: US 8,142,765 B2
(45) Date of Patent: Mar. 27, 2012

(54) COMPOSITION CONTAINING A SEMI-CRYSTALLINE POLYMER AND A VOLATILE OIL

(75) Inventor: Véronique Ferrari, Maisons-Alfort (FR)

(73) Assignee: L'Oreal S.A., Paris (FR)

( * ) Notice: Subject to any disclaimer, the term of this patent is extended or adjusted under 35 U.S.C. 154(b) by 1452 days.

(21) Appl. No.: 10/502,447

(22) PCT Filed: Nov. 6, 2002

(86) PCT No.: PCT/FR02/03801
§ 371 (c)(1),
(2), (4) Date: Mar. 7, 2005

(87) PCT Pub. No.: WO03/061612
PCT Pub. Date: Jul. 31, 2003

(65) Prior Publication Data
US 2005/0142082 A1    Jun. 30, 2005

(30) Foreign Application Priority Data

Jan. 24, 2002 (FR) .................................. 02 00885
Feb. 25, 2002 (FR) .................................. 02 02358

(51) Int. Cl.
*A61K 8/72* (2006.01)
*C08F 290/14* (2006.01)

(52) U.S. Cl. ............................. 424/63; 424/401; 525/50

(58) Field of Classification Search ........................ None
See application file for complete search history.

(56) References Cited

U.S. PATENT DOCUMENTS

| | | | |
|---|---|---|---|
| 3,479,429 A | 11/1969 | Morshauser et al. | |
| 3,937,811 A | 2/1976 | Papantoniou et al. | |
| 4,057,622 A | 11/1977 | Hase et al. | |
| 4,057,623 A | 11/1977 | Hase et al. | |
| 4,083,956 A | 4/1978 | Shelton | |
| 4,423,031 A | 12/1983 | Murui et al. | |
| 4,767,625 A | 8/1988 | Mitsuno et al. | |
| 4,937,069 A | 6/1990 | Shin | |
| 4,996,044 A * | 2/1991 | Mercado et al. ................ | 424/64 |
| 5,034,216 A | 7/1991 | Barone et al. | |
| 5,070,171 A | 12/1991 | O'Lenick, Jr. | |
| 5,091,493 A | 2/1992 | O'Lenick, Jr. et al. | |
| 5,093,452 A | 3/1992 | O'Lenick, Jr. | |
| 5,149,765 A | 9/1992 | O'Lenick, Jr. | |
| 5,156,911 A * | 10/1992 | Stewart ................... | 428/355 AC |
| 5,273,757 A | 12/1993 | Jaeger et al. | |
| 5,302,380 A | 4/1994 | Castrogiovanni et al. | |
| 5,310,547 A | 5/1994 | Dunphy et al. | |
| 5,318,995 A | 6/1994 | Mondet et al. | |
| 5,387,450 A | 2/1995 | Stewart | |
| 5,411,739 A | 5/1995 | Jaeger et al. | |
| 5,474,778 A | 12/1995 | Ichikawa et al. | |
| 5,519,063 A | 5/1996 | Mondet et al. | |
| 5,711,940 A | 1/1998 | Kuentz et al. | |
| 5,736,125 A | 4/1998 | Morawsky et al. | |
| 5,817,304 A | 10/1998 | Mondet et al. | |
| 5,837,223 A | 11/1998 | Barone et al. | |
| 5,843,407 A | 12/1998 | El-Nokaly et al. | |
| 5,851,517 A | 12/1998 | Mougin et al. | |
| 5,866,149 A | 2/1999 | Piot et al. | |
| 5,945,095 A | 8/1999 | Mougin et al. | |
| 6,120,781 A | 9/2000 | Le Bras et al. | |
| 6,132,742 A | 10/2000 | Le Bras et al. | |
| 6,180,123 B1 | 1/2001 | Mondet | |
| 6,254,876 B1 | 7/2001 | De La Poterie et al. | |
| 6,264,933 B1 | 7/2001 | Bodelin et al. | |
| 6,319,508 B1 | 11/2001 | Ribier et al. | |
| 6,464,969 B2 * | 10/2002 | De La Poterie et al. ... | 424/78.03 |
| 6,491,927 B1 | 12/2002 | Arnaud et al. | |
| 6,572,870 B2 | 6/2003 | Ribier et al. | |
| 6,949,504 B2 * | 9/2005 | Mondet et al. ................... | 514/1 |
| 7,019,081 B2 | 3/2006 | Datta et al. | |
| 7,129,276 B2 * | 10/2006 | Ferrari ....................... | 514/772.3 |
| 2002/0164297 A1 | 11/2002 | Ferrari et al. | |
| 2003/0021756 A1 | 1/2003 | Ferrari | |
| 2003/0165451 A1 | 9/2003 | Lennon et al. | |
| 2004/0137028 A1 | 7/2004 | De La Poterie | |
| 2004/0156813 A2 | 8/2004 | Ferrari | |
| 2004/0241118 A1 | 12/2004 | Simon et al. | |

FOREIGN PATENT DOCUMENTS

DE    195 23 478    12/1996

(Continued)

OTHER PUBLICATIONS

Isododecane Material Safety Data Sheet: http://www.bpilabs.com/msds/Isododecane.pdf, accessed Apr. 20, 2009, included with this action.*
Freund et al. (1998). Paraffin products: properties, technologies, applications. p. 267. Accessible online at: http://books.google.com/books?id=SeC-7cx8KKUC&pg=PA267&dq=lipstick+hardness&hl=en&ei=Et7MS8XIMYWgIAfituSfBg&sa=X&oi=book_result&ct=result&resnum=2&ved=0CEMQ6AEwAQ#v=onepage&q=lipstick%20hardness&f=false.*
Isododecane MSDS (see Office Action 20090409).*
Freund et al. (1982). Paraffin products: properties, technologies, applications, p. 267. Accessible online at: http://books.google.com/books?id=SeC-7cx8KKUC&pg=PA3&dq=Freund+paraffin+products+properties+technologies+applications&hl=en&ei=ZPAATfHoClus8AbsgOi1Bw&sa=X&oi=book_result&ct=result&resnum=1&ved=0CCoQ6AEwAA#v=onepage&q=carnauba&f=false.*

(Continued)

*Primary Examiner* — Robert A. Wax
*Assistant Examiner* — H. Sarah Park
(74) *Attorney, Agent, or Firm* — Finnegan, Henderson, Farabow, Garrett & Dunner, LLP

(57) ABSTRACT

The invention relates to a makeup composition comprising a) at least one liquid fatty phase structured with at least one semi-crystalline polymer having an organic structure, whose melting temperature is greater than or equal to 30° C., b) a colorant and c) a volatile oil, the liquid fatty phase, colorant, volatile oil and polymer forming a physiologically acceptable medium.

This composition is in the form in particular of a stick which on keratin materials, particularly the lips, lays down a glossy film which does not undergo transfer to objects with which the keratin materials come into contact.

47 Claims, No Drawings

FOREIGN PATENT DOCUMENTS

| | | |
|---|---|---|
| DE | 195 24 210 | 1/1997 |
| EP | 0206671 A2 | 12/1986 |
| EP | 0 305 756 | 3/1989 |
| EP | 0 367 015 | 5/1990 |
| EP | 0 522 624 | 1/1993 |
| EP | 0 534 823 | 3/1993 |
| EP | 0 549 267 | 6/1993 |
| EP | 0 566 442 | 10/1993 |
| EP | 0 602 902 | 6/1994 |
| EP | 0 667 146 | 8/1995 |
| EP | 0 749 746 | 12/1996 |
| EP | 0 749 747 | 12/1996 |
| EP | 0 873 748 | 10/1998 |
| EP | 0 943 310 | 9/1999 |
| EP | 0 955 039 | 11/1999 |
| EP | 0 979 642 | 2/2000 |
| EP | 0 993 824 | 4/2000 |
| EP | 1 002 528 | 5/2000 |
| EP | 1 034 776 A1 | 9/2000 |
| EP | 1034776 A1 * | 9/2000 |
| EP | 1 332 753 | 8/2003 |
| FR | 2 232 303 | 1/1975 |
| FR | 2 710 646 | 4/1995 |
| FR | 2 842 417 | 9/1998 |
| FR | 2 771 927 | 6/1999 |
| FR | 2 782 917 | 3/2000 |
| FR | 2 824 264 | 11/2002 |
| JP | 61-236716 | 10/1985 |
| JP | 61-289009 | 12/1986 |
| JP | 62-012710 | 1/1987 |
| JP | 04-100534 | 4/1992 |
| JP | 04-210613 | 7/1992 |
| JP | 04-221306 | 8/1992 |
| JP | 9-503785 | 4/1997 |
| JP | 1-233206 | 9/1998 |
| JP | 2000-290138 | 10/2000 |
| SU | 829112 | 5/1981 |
| WO | WO 90/13420 | 11/1990 |
| WO | WO 93/01797 | 2/1993 |
| WO | WO 94/06400 | 3/1994 |
| WO | WO 95/11000 | 4/1995 |
| WO | WO 95/15741 | 6/1995 |
| WO | WO 96/33690 | 10/1996 |
| WO | WO 96/40004 | 12/1996 |
| WO | WO 99/07788 | 2/1999 |
| WO | WO 99/39688 | 8/1999 |
| WO | WO 01/19333 A1 * | 3/2001 |
| WO | WO 02/39961 | 5/2002 |
| WO | WO 2004/041150 | 5/2004 |

OTHER PUBLICATIONS

Machine translation of EP1034776-A1 (see Office Action of Apr. 28, 2010).*
English language Derwent Abstract of EP 1 034 776 A1, Sep. 13, 2000.
English language Derwent Abstract of JP 2000-290138.
Boutevin, B. et al., "Study of Morphological and Mechanical Properties of PP/PBT Blends," Polymer Bulletin, 34, pp. 117-123, (1995).
Dweck, "The Sweating of Lipsticks," Cosmetics & Toiletries, vol. 96, pp. 29-32 (Jan. 1981).
English language Derwent Abstract of DE 195 23 478.
English language Derwent Abstract of DE 195 24 210.
English language Derwent Abstract of EP 0 566 442.
English language Derwent Abstract of EP 0 873 748.
English language Derwent Abstract of EP 0 943 310.
English language Derwent Abstract of EP 0 979 642.
English language Derwent Abstract of EP 0 993 824.
English language Derwent Abstract of FR 2 771 927.
English language Derwent Abstract of FR 2 782 917.
English language Derwent Abstract of JP 1-233206.
English language Derwent Abstract of JP 61-236716.
English language Derwent Abstract of SU 829112.
French Search Report for FR 04/06173 (Priority Application for U.S. Appl. No. 11/147,236), dated Jan. 31, 2005.
Grulke, E., "Solubility Parameter Values," Polymer Handbook, Third Edition, John Wiley & Sons, 1989, pp. 519-559.
Hamley, I.W., "Crystallization in Block Copolymers," Advances in Polymer Science, vol. 148, pp. 113-137 (1999).
Hansen, C.M., "The Three Dimensional Solubility Parameter—Key to Paint Component Affinities: I. Solvents, Plasticizers, Polymers, and Resins," Journal of Paint Technology, vol. 39, No. 505, pp. 104-117 (1967).
International Search Report for PCT/FR02/03802, dated Apr. 28, 2003.
Material Data Safety Sheet, Rheox, Inc., pp. 5-7, 9-11 (1992).
Matsuda, et al.,"Solid-Liquid Separation Phenomenon on the Surface of an Oil," Wax and Pigments Mixture (I) a Binary Oil-Wax System, Shikizai, vol. 57 (3), pp. 1-13 (1984).
Nojima, S. et al., "Melting Behavior of Poly (e-caprolactone)-block-Polybutadiene Copolymers," Macromolecules, vol. 32, No. 11, pp. 3727-3734 (1999).
Office Action mailed Apr. 23, 2009, in U.S. Appl. No. 10/502,448.
Rangarajan P., et al., "Morphology of Semi-Crystalline Block Copolymers of Ethylene-(ethylene-alt-propylene)," Macromolecules, 26, 4640-4645 (1993).
Richter, P. et al., "Polymer Aggregates with Crystalline Cores: The System Poly(ethylene)-poly(ethylene-propylene)," Macromolecules, 30, 1053-1068 (1997).
U.S. Appl. No. 11/147,236, filed Jun. 8, 2005.
U.S. Appl. No. 10/502,448, filed Feb. 15, 2005.
Van Ham, et al., "Lipstick Formula Variations and Lipstick Properties," Cosmetics and Perfumery, vol. 90, pp. 27,28,30,32,34 (1975).
Office Action mailed Apr. 28, 2010, in co-pending U.S. Appl. No. 10/502,448.

* cited by examiner

COMPOSITION CONTAINING A SEMI-CRYSTALLINE POLYMER AND A VOLATILE OIL

This application is a national stage application of International Application No. PCT/FRO2/03801, filed Nov. 6, 2002, which claims priority to French Application Nos. FR 02/00885 and FR 02/02358, filed on Jan. 24, 2002, and Feb. 25, 2002, respectively.

The present invention relates to a composition, particularly a cosmetic composition, comprising at least one semi-crystalline polymer and a volatile oil, which is in the form in particular of a stick and whose application leads to a glossy and comfortable coating which does not undergo transfer.

Cosmetic compositions whose fatty phase is gelled using semi-crystalline polymers have been described in the as yet unpublished application FR 0106047. However, these compositions for application to the lips, when applied to the skin, present the drawback of undergoing transfer, in other words of at least partly depositing—leaving a mark—on certain substrates with which they may be brought into contact, and in particular a glass, an item of clothing, or the skin. The consequence is mediocre persistence of the film on the lips and hence the necessity to repeat application of the lipstick composition at regular intervals.

At the same time, users of non-transfer lipsticks often complain of the lack of comfort and gloss of these types of formulas—formulas which, otherwise, exhibit very good staying power.

Improving the performance of non-transfer lipsticks is a problem that a number of cosmeticians have attempted to solve. Reference may be made accordingly to Shiseido (JP-A-61-65809), Procter & Gamble (WO-A-96/40004) or Revlon (U.S. Pat. No. 5,837,223).

In application FR-A-2 804 018, L'Oreal described the combination of volatile solvent with heteroatom polymers of the polyamide type. These compositions, however, which lead to lipsticks whose coating does not undergo transfer and is glossy, have the drawback of presenting a stickiness which can be a critical flaw and adjudged uncomfortable.

An aim of the present invention is to overcome these drawbacks and the invention proposes a composition which allows a film to be obtained that has very good staying power, does not undergo transfer, and whose gloss is enhanced relative to the non-transfer compositions of the prior art.

Surprisingly the applicant has found that the addition of a volatile oil to a composition comprising a semi-crystalline polymer allows a non-transfer composition to be obtained whose gloss is enhanced.

The invention applies in particular to lip makeup products but also to eye makeup products, such as eyeliners, in particular in pencil form, and mascaras, in particular in block form, or skin makeup products, such as foundations.

More specifically the invention provides a makeup composition comprising a) at least one liquid fatty phase structured with at least one semi-crystalline polymer having an organic structure and a melting temperature of greater than or equal to 30° C., b) a colorant and c) a volatile oil, the liquid fatty phase, colorant, volatile oil and polymer forming a physiologically acceptable medium.

The melting temperature of the semi-crystalline polymer is preferably less than 150° C.

The composition of the invention may be in the form of a paste, a solid or a cream. It may be an oil-in-water emulsion or a water-in-oil emulsion, or a solid or soft anhydrous gel. It is preferably in anhydrous form, and more especially in the form of an anhydrous gel, especially cast as a stick or as a dish.

For the purposes of the invention, the term "semi-crystalline polymer" means polymers comprising a crystallizable portion and an amorphous portion in the skeleton and having a first-order reversible change of phase temperature, in particular of melting (solid-liquid transition). The crystallizable portion is either a side chain (or pendent chain) or a block in the skeleton.

For the purposes of the present invention, the term "polymers" means compounds containing at least 2 repeating units, preferably at least 3 repeating units and more especially at least 10 repeating units.

When the crystallizable portion is a block of the polymer skeleton, this crystallizable block has a different chemical nature to that of the amorphous blocks; in this case, the semi-crystalline polymer is a block copolymer, for example of the diblock, triblock or multiblock type. When the crystallizable portion is a chain that is pendent on the skeleton, the semi-crystalline polymer may be a homopolymer or a copolymer.

The terms "organic compound" and "having an organic structure" mean compounds containing carbon atoms and hydrogen atoms, and possibly heteroatoms such as S, O, N or P, alone or in combination.

Semi-Crystalline Polymers

The semi-crystalline polymer(s) of the composition of the invention advantageously comprise a weight-average molecular mass Mw ranging from 5,000 to 1,000,000, preferably from 10,000 to 800,000 and preferentially from 15,000 to 500,000.

The semi-crystalline polymer(s) according to the invention serving as structuring agent are solids at ambient temperature (25° C.) and atmospheric pressure (760 mmHg), with a melting temperature of greater than or equal to 30° C. The melting point values correspond to the melting point measured using a differential scanning calorimeter (DSC), such as the calorimeter sold under the name DSC 30 by the company Mettler, with a temperature rise of 5 or 10° C. per minute (the melting point under consideration is the point corresponding to the temperature of the most endothermic peak of the thermogram).

The semi-crystalline polymer(s) according to the invention preferably have a melting temperature greater than the temperature of the keratinous support intended for receiving the said composition, in particular the skin or the lips.

The semi-crystalline polymer(s) according to the invention are capable, alone or as a mixture, of structuring the composition without the addition of a particular surfactant or of filler or of wax.

According to the invention, the semi-crystalline polymers are advantageously soluble in the fatty phase, especially to at least 1% by weight, at a temperature greater than their melting temperature. Besides the crystallizable chains or blocks, the blocks of the polymers are amorphous.

For the purposes of the invention, the expression "crystallizable chain or block" means a chain or block which, if it were alone, would change from the amorphous state to the crystalline state reversibly, depending on whether one is above or below the melting temperature. For the purposes of the invention, a "chain" is a group of atoms, pendent or lateral relative to the polymer skeleton. A "block" is a group of atoms belonging to the skeleton, this group constituting one of the repeating units of the polymer.

Preferably, the polymer skeleton of the semi-crystalline polymers is soluble in the liquid fatty phase.

Preferably, the crystallizable blocks or chains of the semi-crystalline polymers represent at least 30% of the total weight of each polymer and better still at least 40%. The semi-crystalline polymers containing crystallizable side chains are homopolymers or copolymers. The semi-crystalline polymers of the invention containing crystallizable blocks are block or multiblock copolymers. They may be obtained by polymerizing a monomer containing reactive (or ethylenic) double bonds or by polycondensation. When the polymers of the invention are polymers containing crystallizable side chains, these side chains are advantageously in random or statistical form.

Preferably, the semi-crystalline polymers of the invention are of synthetic origin. Moreover, they do not comprise a polysaccharide skeleton.

The semi-crystalline polymers useful in the invention are in particular:
- block copolymers of polyolefins of controlled crystallization, whose monomers are described in EP-A-0 951 897,
- polycondensates, especially of aliphatic or aromatic polyester type or of aliphatic/aromatic polyester type,
- homopolymers or copolymers bearing at least one crystallizable side chain and homopolymers or copolymers bearing in the skeleton at least one crystallizable block, such as those described in document U.S. Pat. No. 5,156,911,
- homopolymers or copolymers bearing at least one crystallizable side chain, in particular bearing fluoro group(s), as described in document WO-A-01/19333,
- and mixtures thereof. In these last two cases, the crystallizable side chain(s) or block(s) are hydrophobic.

A) Semi-Crystalline Polymers Containing Crystallizable Side Chains

Mention may be made in particular of those defined in documents U.S. Pat. No. 5,156,911 and WO-A-01/19333.

They are homopolymers or copolymers comprising from 50% to 100% by weight of units resulting from the polymerization of one or more monomers bearing a crystallizable hydrophobic side chain.

These homopolymers or copolymers are of any nature, provided that they meet the conditions mentioned hereinbelow with, in particular, the characteristic of being soluble or dispersible in the liquid fatty phase, by heating above their melting temperature mp. They can result:
- from the polymerization, especially the free-radical polymerization, of one or more monomers containing reactive or ethylenic double bond(s) with respect to a polymerization, namely a vinyl, (meth)acrylic or allylic group,
- from the polycondensation of one or more monomers bearing co-reactive groups (carboxylic acid, sulphonic acid, alcohol, amine or isocyanate), such as, for example, polyesters, polyurethanes, polyethers, polyureas or polyamides.

a) In general, the crystallizable units (chains or blocks) of semi-crystalline polymers according to the invention are derived from monomer(s) containing crystallizable block(s) or chain(s), used for manufacturing semi-crystalline polymers. These polymers are selected especially from homopolymers and copolymers resulting from the polymerization of at least one monomer containing crystallizable chain(s) that may be represented by formula X:

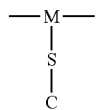

with M representing an atom of the polymer skeleton,
S representing a spacer and
C representing a crystallizable group.

The crystallizable chains "—S—C" may be aliphatic or aromatic, and optionally fluorinated or perfluorinated. "S" especially represents a group $(CH_2)_n$ or $(CH_2CH_2)_n$ or $(CH_2O)$, which is linear or branched or cyclic, with n being an integer ranging from 0 to 22. Preferably, "S" is a linear group. Preferably, "S" and "C" are different.

When the crystallizable chains are hydrocarbon-based aliphatic chains, they comprise hydrocarbon-based alkyl chains containing at least 11 carbon atoms and not more than 40 carbon atoms and better still not more than 24 carbon atoms. They are especially aliphatic chains or alkyl chains containing at least 12 carbon atoms, and they are preferably $C_{14}$-$C_{24}$, preferably $C_{16}$-$C_{22}$ alkyl chains. When they are fluoroalkyl or perfluoroalkyl chains, they contain at least 11 carbon atoms, at least 6 of which carbon atoms are fluorinated.

As examples of semi-crystalline homopolymers or copolymers containing crystallizable chain(s), mention may be made of those resulting from the polymerization of one or more of the following monomers: saturated alkyl (meth)acrylates with the alkyl group being $C_{14}$-$C_{24}$, perfluoroalkyl (meth)acrylates with a $C_{11}$-$C_{15}$ perfluoroalkyl group, N-alkyl (meth)acryl-amides with the alkyl group being $C_{14}$ to $C_{24}$ with or without a fluorine atom, vinyl esters containing alkyl or perfluoro(alkyl) chains with the alkyl group being $C_{14}$ to $C_{24}$ (with at least 6 fluorine atoms per perfluoroalkyl chain), vinyl ethers containing alkyl or perfluoro(alkyl) chains with the alkyl group being $C_{14}$ to $C_{24}$ and at least 6 fluorine atoms per perfluoroalkyl chain, $C_{14}$ to $C_{24}$ alpha-olefins such as, for example, octadecene, para-alkylstyrenes with an alkyl group containing from 12 to 24 carbon atoms, and mixtures thereof.

When the polymers result from a polycondensation, the hydrocarbon-based and/or fluorinated crystallizable chains as defined above are borne by a monomer that may be a diacid, a diol, a diamine or a diisocyanate.

When the polymers that are the subject of the invention are copolymers, they additionally contain from 0 to 50% of groups Y or Z resulting from the copolymerization:
α) of Y, which is a polar or non-polar monomer or a mixture of the two:
When Y is a polar monomer, it is either a monomer bearing polyoxyalkylenated groups (especially oxyethylenated and/or oxypropylenated groups), a hydroxyalkyl (meth)acrylate, for instance hydroxyethyl acrylate, (meth)acrylamide, an N-alkyl (meth)acrylamide, an N,N-dialkyl(meth)acrylamide such as, for example, N,N-diisopropylacrylamide or N-vinylpyrrolidone (NVP), N-vinylcaprolactam, a monomer bearing at least one carboxylic acid group, for instance (meth)acrylic acid, crotonic acid, itaconic acid, maleic acid or fumaric acid, or bearing a carboxylic acid anhydride group, for instance maleic anhydride, and mixtures thereof.
When Y is a non-polar monomer, it may be an ester of the linear, branched or cyclic alkyl (meth)acrylate type, a vinyl ester, an alkyl vinyl ether, an alpha-olefin, styrene or styrene substituted with a $C_1$ to $C_{10}$ alkyl group, for instance α-methylstyrene, or a macromonomer of the polyorganosiloxane type containing vinyl unsaturation.

For the purposes of the invention, the term "alkyl" means a saturated group especially of $C_8$ to $C_{24}$, except where otherwise mentioned.

β) of Z, which is a polar monomer or a mixture of polar monomers. In this case, Z has the same definition as the "polar Y" defined above.

Preferably, the semi-crystalline polymers containing a crystallizable side chain are alkyl (meth)acrylate or alkyl (meth)acrylamide homopolymers with an alkyl group as defined above, and especially of $C_{14}$-$C_{24}$, copolymers of these monomers with a hydrophilic monomer preferably of different nature from (meth)acrylic acid, for instance N-vinylpyrrolidone or hydroxyethyl (meth)acrylate, and mixtures thereof.

B) Polymers Bearing in the Skeleton at Least One Crystallizable Block

This is also a case of polymers that are soluble or dispersible in the liquid fatty phase by heating above their melting point mp. These polymers are especially block copolymers consisting of at least two blocks of different chemical nature, one of which is crystallizable.

The polymers defined in patent U.S. Pat. No. 5,156,911 may be used.

Block copolymers of olefin or of cycloolefin containing a crystallizable chain, for instance those derived from the block polymerization of:

cyclobutene, cyclohexene, cyclooctene, norbornene (i.e. bicyclo(2.2.1)hept-2-ene), 5-methylnorbornene, 5-ethylnorbornene, 5,6-dimethylnorbornene, 5,5,6-trimethylnorbornene, 5-ethylidenenorbornene, 5-phenylnorbornene, 5-benzylnorbornene, 5-vinylnorbornene, 1,4,5,8-dimethano-1,2,3,4,4a,5,8a-octahydronaphthalene, dicyclopentadiene, or mixtures thereof, with ethylene, propylene, 1-butene, 3-methyl-1-butene, 1-hexene, 4-methyl-1-pentene, 1-octene, 1-decene or 1-eicosene, or mixtures thereof, and in particular copoly(ethylene/norbornene) blocks and (ethylene/propylene/ethylidenenorbornene) block terpolymers. Those resulting from the block copolymerization of at least 2 $C_2$-$C_{16}$, better still $C_2$-$C_{12}$, α-olefins such as those mentioned above and in particular block bipolymers of ethylene and of 1-octene may also be used.

The copolymers may be copolymers containing at least one crystallizable block, the rest of the copolymer being amorphous (at ambient temperature). These copolymers may also contain two crystallizable blocks of different chemical nature. The preferred copolymers are those that simultaneously contain at ambient temperature a crystallizable block and an amorphous block that are both hydrophobic and lipophilic, sequentially distributed; mention may be made, for example, of polymers containing one of the crystallizable blocks and one of the amorphous blocks below:

Block that is crystallizable by nature: a) polyester, for instance poly(alkylene terephthalate)s, b) polyolefin, for instance polyethylenes or polypropylenes.

Amorphous and lipophilic block, for instance: amorphous polyolefins or copoly(olefin)s such as poly(isobutylene), hydrogenated polybutadiene or hydrogenated poly(isoprene).

As examples of such copolymers containing a crystallizable block and an amorphous block, mention may be made of:

α) poly(ε-caprolactone)-b-poly(butadiene) block copolymers, preferably used hydrogenated, such as those described in the article D6 "Melting behaviour of poly(ε-caprolactone)-block-polybutadiene copolymers" from S. Nojima, Macromolecules, 32, 3727-3734 (1999), β) the hydrogenated block or multiblock poly(butylene terephthalate)-b-poly(isoprene) block copolymers cited in the article D7 "Study of morphological and mechanical properties of PP/PBT" by B. Boutevin et al., Polymer Bulletin, 34, 117-123 (1995), γ) the poly(ethylene)-b-copoly(ethylene/propylene) block copolymers cited in the articles D8 "Morphology of semi-crystalline block copolymers of ethylene-(ethylene-alt-propylene)" by P. Rangarajan et al., Macromolecules, 26, 4640-4645 (1993) and D9 "Polymer aggregates with crystalline cores: the system poly(ethylene)-poly(ethylene-propylene)" by P. Richter et al., Macromolecules, 30, 1053-1068 (1997), δ) the poly(ethylene)-b-poly(ethylethylene) block copolymers cited in the general article D10 "crystallization in block copolymers" by I. W. Hamley, Advances in Polymer Science, Vol. 148, 113-137 (1999).

The semi-crystalline polymers in the composition of the invention may or may not be partially crosslinked, provided that the degree of crosslinking does not interfere with their dissolution or dispersion in the liquid fatty phase by heating above their melting temperature. It may then be a chemical crosslinking, by reaction with a polyfunctional monomer during the polymerization. It may also be a physical crosslinking which may, in this case, be due either to the establishment of bonds of hydrogen or dipolar type between groups borne by the polymer, such as, for example, the dipolar interactions between carboxylate ionomers, these interactions being of small amount and borne by the polymer skeleton; or to a phase separation between the crystallizable blocks and the amorphous blocks borne by the polymer.

Preferably, the semi-crystalline polymers in the composition according to the invention are non-crosslinked.

As specific examples of the structuring semi-crystalline polymer that may be used in the composition according to the invention, mention may be made of the products Intelimer® from the company Landec, described in the brochure "Intelimer® polymers", Landec IP22 (Rev. 4-97). These polymers are in solid form at ambient temperature (25° C.). They bear crystallizable side chains and have the formula X above.

Mixture of High-melting Semi-crystalline Polymer and Low-melting Semi-crystalline Polymer In the description hereinbelow, the semi-crystalline polymer(s) with a melting temperature $mp_2$ of less than 50° C. will be referred to as "low-melting polymers" and the crystalline or semi-crystalline compound(s) with a melting temperature $mp_1$ of greater than or equal to 50° C. will be referred to as "high-melting compounds". According to the invention, the melting point may be measured especially by any known method and in particular using a differential scanning calorimeter (DSC).

The composition advantageously comprises a mixture of a polymer selected from low-melting polymers having a melting temperature of less than 50° C. and of a polymer selected from high-melting polymers having a melting temperature of at least 50° C.

According to the invention, the high-melting semi-crystalline compound(s) are advantageously polymers with a melting temperature $mp_1$ such that 50° C.$\leq mp_1 \leq$150° C., better still 55° C.$\leq mp_1 \leq$150° C., and preferably 60° C.$\leq mp_1 \leq$130° C., and the low-melting polymers advantageously have a melting temperature $mp_2$ such that 30°

C.≦$mp_2$≦50° C. and better still 35° C.≦$mp_2$≦45° C. This melting temperature is a first-order change of state temperature.

In general the low-melting polymers have a melting temperature $mp_2$ at least equal to the temperature of the keratinous support intended for receiving the composition according to the invention.

As high-melting compounds that may be used in the invention, mention may be made of high-melting waxes, for instance certain polyethylene waxes such as Epolene N-14 sold by Eastman Chemical Cie., carnauba waxes and certain microcrystalline waxes, for instance those sold by Tisco under the brand name "Tisco wax 88", and also high-melting semi-crystalline polymers. Preferably, the high-melting compound is a second high-melting organic solid semi-crystalline polymer. However, it is possible to use, as high-melting compound, crystalline polymers that are solid at ambient temperature, having a melting temperature of greater than 50° C., random polymers comprising a controlled crystallization, as described in document EP-A-0 951 897, and more particularly the commercial products Engage 8 401 and Engage 8 402 from DuPont de Nemours, with melting temperatures of 51° C. and 64° C. respectively, which are ethylene/1-octene random biopolymers.

i) The semi-crystalline polymers with a melting point of less than 50° C. are especially those described in Examples 3, 4, 5, 7 and 9 of patent U.S. Pat. No. 5,156,911, containing a —COOH group, resulting from the copolymerization of acrylic acid and of a $C_5$ to $C_{16}$ alkyl (meth)acrylate with a melting temperature ranging from 20° C. to 35° C., and more particularly from the copolymerization:
of acrylic acid, of hexadecyl acrylate and of isodecyl acrylate in a 1/16/3 ratio,
of acrylic acid and of pentadecyl acrylate in a 1/19 ratio,
of acrylic acid, of hexadecyl acrylate and of ethyl acrylate in a 2.5/76.5/20 ratio,
of acrylic acid, of hexadecyl acrylate and of methyl acrylate in a 5/85/10 ratio,
of acrylic acid and of polyoctadecyl methacrylate in a 2.5/97.5 ratio.

It is also possible to use the polymer Structure "O" from National Starch, such as the product described in document U.S. Pat. No. 5,736,125 with a melting temperature of 44° C., and also the semi-crystalline polymers with crystallizable pendent chains comprising fluoro groups, as described in Examples 1, 4, 6, 7 and 8 of document WO-A-01/19333.

It is also possible to use the low-melting semi-crystalline polymers obtained by copolymerization of stearyl acrylate and of acrylic acid or of NVP, as described in document U.S. Pat. No. 5,519,063 or EP-A-550 745 and more especially those described in Examples 1 and 2 below, of polymer preparation.

ii) The semi-crystalline polymers with a melting point of greater than or equal to 50° C. are especially the Intelimer described in the brochure "Intelimer® polymers", Landec IP22 (Rev. 4-97) with a melting temperature of 56° C., which is an impermeable, non-sticky product that is viscous at ambient temperature.

It is also possible to use semi-crystalline polymers obtained by copolymerization of behenyl acrylate and of acrylic acid or of NVP, as described in documents U.S. Pat. No. 5,519,063 and EP-A-0 550 745, and more especially those described in Examples 3 and 4 below, of polymer preparation.

Preferably, the low-melting semi-crystalline polymers and/or those with a high melting point do not comprise a carboxylic group.

According to the invention and advantageously, the high-melting compound (crystalline or semi-crystalline) and the low-melting compound are in a weight ratio ranging from 10/90 to 90/10, better still from 40/60 to 60/40 and more preferably in a weight ratio of close to 50/50.

Advantageously, the weight ratio of semi-crystalline polymer having an organic structure relative to the liquid fatty phase is from 0.20 to 0.60 and better still from 0.25 to 0.50, so as to obtain a hard stick that breaks down on contact with the skin or the lips, in particular having a hardness ranging from 100 to 350 gf.

The gelation of the fatty phase may be adjusted depending on the nature of the polymer(s) and their respective concentrations, and may be such that a rigid structure in the form of a tube or a stick is obtained.

The content of each polymer is chosen according to the desired hardness of the composition and as a function of the particular application intended. The respective amounts of polymer may be such that they allow the production of a solid that can be broken down, in particular having a hardness ranging from 100 to 350 gf. This hardness may be measured by the "cheesewire" method, which consists in cutting a tube of lipstick 12.7 mm in diameter and in measuring the hardness at 20° C., using a DFGHS 2 tensile testing machine from the company Indelco-Chatillon, travelling at a speed of 100 mm/minute. It is expressed as the shear force (expressed as gram-force) required to cut a stick under these conditions.

This hardness is such that the composition is self-supporting and can be broken down easily to form a satisfactory deposit on the skin and the lips. In addition, with this hardness, the composition of the invention in cast form, especially in the form of a stick, shows good impact strength.

The composition of the invention is preferably in the form of a solid stick with a hardness ranging from 100 gf to 350 gf, measured according to the "cheesewire" method. However, it is possible to use an amount of semi-crystalline polymer such that the composition is in the form of a soft paste that can be applied by finger or by using an applicator to keratin materials.

In practice, the total amount of semi-crystalline polymer(s) represents from 0.1% to 80%, better still from 0.5% to 40% and even better still from 3% to 30% of the total weight of the composition. It preferably represents from 15% to 25% by weight of the composition.

The tubes or sticks according to the invention produce, after application, a glossy, non-sticky coating of uniform colour that gives good coverage (i.e. the skin or the lips do not show through the makeup).

Volatile Oil

By "volatile oil" is meant any non-aqueous medium that is liable to evaporate on contact with the skin in less than one hour, at ambient temperature (25° C.) and atmospheric pressure (760 mmHg).

The volatile cosmetic oil or oils which are liquid at ambient temperature have in particular a vapour pressure, measured at ambient temperature and atmospheric pressure, ranging from $10^{-3}$ to 300 mmHg (0.266 Pa to 40,000 Pa), preferably from 0.02 mmHg to 300 mmHg (2.66 Pa to 40,000 Pa) and more preferably ranging from 0.1 to 90 mmHg (13 Pa to 12,000 Pa).

According to the invention these volatile oils facilitate in particular the application of the composition to the skin, lips or epidermal derivatives. These oils may be hydrocarbon-based oils, silicone oils optionally containing alkyl or alkoxy groups, pendent or at the end of the silicone chain, or a mixture of these oils.

Preferably, the volatile oils are cosmetic oils selected from oils having no flash point, oils having a flash point ranging from 40° C. to 100° C., and mixtures thereof, for the purpose of making it easier to employ them. Moreover, they advantageously have a boiling temperature at atmospheric pressure of less than 220° C. and more preferably less than 210° C., in particular ranging from 110 to 210° C. Preferably, these volatile oils are not monoalcohols containing at least 7 carbon atoms.

As volatile oils which can be used in the invention mention may be made of linear or cyclic silicone oils having a viscosity at ambient temperature of less than 8 cSt and having in particular from 2 to 7 silicon atoms, these silicones optionally containing alkyl or alkoxy groups having from 1 to 10 carbon atoms. As volatile silicone oil which can be used in the invention mention may be made in particular of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyl-tetrasiloxane, dodecamethylpentasiloxane and mixtures thereof.

As other volatile oil which can be used in the invention mention may be made of volatile hydrocarbon-based oils having from 8 to 16 carbon atoms and mixtures thereof, and in particular branched $C_8$-$C_{16}$ alkanes, for instance $C_8$-$C_{16}$ isoalkanes (also called isoparaffins), isododecane, isodecane, isohexadecane, and, for example, the oils sold under the trade names of Isopars or Permetyls, branched $C_8$-$C_{16}$ esters such as isohexyl neopentanoate, and mixtures thereof.

Preference is given to using isododecane (Permetyls 99 A), $C_8$-$C_{16}$ isoparaffins such as Isopar L, E, G or H, mixtures thereof, optionally in combination with decamethyltetrasiloxane or with cyclopentasiloxane.

It is also possible to use volatile fluoro oils.

These volatile oils represent in particular from 5% to 97.5% of the total weight of the composition, and better still from 10% to 75%, more preferably between 20% and 50%, of the total weight of the composition. Generally speaking, the amount of volatile solvent used is sufficient to obtain non-transfer properties. This amount will be adapted by the person skilled in the art in accordance with the desired intensity of the non-transfer properties.

The volatile oil preferably represents from 20% to 50% by weight of the composition, preferably from 30% to 40%, preferably approximately 35%.

The volatile oil preferably represents from 40% to 60% of the liquid fatty phase, preferably from 45% to 55%.

The weight ratio of volatile oil relative to the semi-crystalline polymer is advantageously between 1 and 2.5, preferably from 1.5 to 2.

Liquid Fatty Phase

For the purposes of the patent application, the term "liquid fatty phase" means a fatty phase that is liquid at ambient temperature (25° C.) and atmospheric pressure (760 mmHg), composed of one or more mutually compatible fatty substances that are liquid at ambient temperature, also known as oils. This fatty phase is macroscopically homogeneous.

Advantageously, the liquid fatty phase, structured with the semi-crystalline polymers, constitutes the continuous phase of the composition. This fatty phase may contain one or more apolar or non-polar oils or a mixture of apolar oil(s) and of polar oil(s) or a mixture of polar oils, other than the aliphatic alcohol described above.

The apolar oils according to the invention are in particular silicone oils such as linear or cyclic polydimethylsiloxanes (PDMS) which are liquid at ambient temperature; polydimethylsiloxanes containing alkyl, alkoxy or phenyl groups, pendent and/or at the end of a silicone chain, these groups containing from 2 to 24 carbon atoms and being liquid at ambient temperature; phenyl silicones, for instance phenyl trimethicones, phenyl dimethicones, phenyl trimethylsiloxy diphenylsiloxanes, diphenyl dimethicones, diphenyl methyldiphenyl trisiloxanes, and 2-phenylethyl trimethylsiloxysilicates, which are liquid; linear or branched hydrocarbons or fluorocarbons of synthetic or mineral origin, which are liquid, for instance liquid paraffins and derivatives thereof, petroleum jelly, polydecenes, hydrogenated polyisobutene such as Parleam® sold by the company Nippon Oil Fats, and squalane; and mixtures thereof. Preferably, the apolar oils used are liquid apolar oils of the hydrocarbon-based type, of mineral or synthetic origin, chosen especially from Parleam® oil (hydrogenated isoparaffin), isoparaffins and squalane, and mixtures thereof.

The liquid fatty phase advantageously comprises at least one polar oil and at least one sparingly polar oil, for instance isononyl isononanoate.

In particular, the polar oils of the invention are:
hydrocarbon-based plant oils with a high content of triglycerides consisting of fatty acid esters (of $C_8$ to $C_{24}$) of glycerol in which the fatty acids may have varied chain lengths, these chains possibly being linear or branched, and saturated or unsaturated; these oils are, in particular, wheatgerm oil, corn oil, sunflower oil, shea butter, castor oil, sweet-almond oil, macadamia oil, apricot oil, soybean oil, rapeseed oil, cotton oil, alfalfa oil, poppy oil, pumpkin oil, sesame oil, marrow oil, avocado oil, hazelnut oil, grapeseed oil, blackcurrant seed oil, evening primrose oil, millet oil, barley oil, quinoa oil, olive oil, rye oil, safflower oil, candlenut oil, passionflower oil and musk rose oil; or alternatively caprylic/capric acid triglycerides such as those sold by the company Stearineries Dubois or those sold under the names Miglyol 810, 812 and 818 by the company Dynamit Nobel;
synthetic oils of formula $R_5COOR_6$ in which $R_5$ represents a linear or branched higher fatty acid residue containing from 7 to 40 carbon atoms and $R_6$ represents a branched hydrocarbon-based chain containing from 3 to 40 carbon atoms, such as, for example, purcellin oil (cetostearyl octanoate), isononyl isononanoate and $C_{12}$ to $C_{15}$ alcohol benzoate;
synthetic esters and ethers, for instance isopropyl myristate, 2-ethylhexyl palmitate, alcohol or polyalcohol octanoates, decanoates or ricinoleates, and hydroxylated esters, for instance isostearyl lactate or diisostearyl malate; and pentaerythritol esters;
fatty acids containing from 12 to 22 carbon atoms such as oleic acid, linoleic acid or linolenic acid;
mixtures thereof.

The liquid fatty phase represents, in practice, from 5% to 99% and preferably from 20% to 80% of the total weight of the composition. It advantageously represents at least 60% of the total weight of the composition.

Colorant

The composition advantageously comprises a colorant, which may be selected from the lipophilic dyes, hydrophilic dyes, pigments and nacres usually used in cosmetic or dermatological compositions, and mixtures thereof. This colorant is generally present in a proportion of from 0.01% to 50% (solids), and preferably from 5% to 30%, of the total weight of the composition (if present).

The fat-soluble dyes are, for example, Sudan Red, D&C Red 17, D&C Green 6, β-carotene, soybean oil, Sudan Brown, D&C Yellow 11, D&C Violet 2, D&C Orange 5, quinoline yellow and annatto. They can represent from 0% to 20% of the weight of the composition and better still from 0.01% to 6% (if present). The water-soluble dyes are, for example, beetroot juice or methylene blue, and can represent up to 6% of the total weight of the composition.

The pigments may be white or coloured, mineral and/or organic, and coated or uncoated. Among the mineral pigments which may be mentioned are titanium dioxide or zinc dioxide, optionally surface-treated, zirconium oxide or cerium oxide, as well as iron oxides, chromium oxide, manganese violet, ultramarine blue, chromium hydrate and ferric blue. Among the organic pigments which may be mentioned are carbon black, pigments of D&C type, and lakes based on cochineal carmine or on barium, strontium, calcium or aluminium (such as D&C Red 27, 21 or 7, D&C Yellow 5 or 6 and FD&C Blue No. 1). The pigments can represent from 0 to 40% (0.01% to 40%), especially from 0.5% to 35% and better still from 2% to 25% of the total weight of the composition (if present).

The nacreous pigments may be chosen from white nacreous pigments such as mica, especially mica coated with titanium or with bismuth oxychloride, coloured nacreous pigments such as titanium mica with iron oxides, titanium mica with, in particular, ferric blue or chromium oxide, titanium mica with an organic pigment of the type mentioned above, and also nacreous pigments based on bismuth oxychloride. They can represent from 0% to 25% (0.05% to 25%) and better still from 0.1% to 15% of the total weight of the composition (if present).

Advantageously, the pigments and nacres are introduced into the composition in the form of a pigment paste.

For the purposes of the invention, the term "pigment paste" means a concentrated colloidal dispersion of coated or uncoated coloured particles in a continuous medium, optionally stabilized using a dispersant.

As will be appreciated, the person skilled in the art will take care to select the optional additional additives and/or the amount thereof such that the advantageous properties of the composition according to the invention are not, or are not substantially, adversely affected by the envisaged addition.

The makeup composition of the invention may be in the form of a coloured product, in particular for the skin, optionally having care or treatment properties, and may be in particular a foundation, a blusher, a rouge, an eyeshadow, a concealer product, an eyeliner or a body makeup product; a lip makeup product, for instance a lipstick, a lipgloss or a lip pencil, optionally with care or treatment properties; a makeup product for the epidermal derivatives, for instance the nails, for the eyelashes in the form of a mascara, or for the eyebrows and the hair. It is preferably anhydrous or in cast form.

As will be appreciated, the composition of the invention must be cosmetically acceptable, i.e. it must contain a physiologically acceptable non-toxic medium and must be able to be applied to human skin, epidermal derivatives or lips of the face. For the purposes of the invention, the expression "cosmetically acceptable" means a composition of pleasant appearance, odour, feel and, where appropriate, taste.

At least one wax such as those used hithero in cosmetics may also be used in the composition of the invention.

For the purposes of the present invention, a wax is a lipophilic fatty compound that is solid at ambient temperature (25° C.) and atmospheric pressure (760 mmHg), which undergoes a reversible solid/liquid change of state, having a melting temperature of greater than 40° C. and better still greater than 50° C., which may range up to 200° C., and having an anisotropic crystalline organization in the solid state. The size of the crystals is such that the crystals diffract and/or scatter light, giving the composition a cloudy, more or less opaque appearance. By bringing the wax to its melting temperature, it is possible to make it miscible with oils and to form a microscopically homogeneous mixture, but, on returning the temperature of the mixture to ambient temperature, recrystallization of the wax in the oils of the mixture is obtained. This recrystallization in the mixture may be responsible for the reduction in the gloss of the said mixture. Thus the composition advantageously contains little or no standard waxes, and especially less than 10% by weight and better still less than 5% of standard wax relative to the total weight of the composition.

For the purposes of the patent application, the standard waxes are those generally used in cosmetology and dermatology; they are especially of natural origin, for instance beeswax, candelilla wax, ouricury wax, Japan wax, cork fibre wax, sugarcane wax, paraffin wax, lignite wax, microcrystalline waxes with a melting point >50° C., lanolin wax, montan wax, ozokerites and hydrogenated oils such as hydrogenated jojoba oil, but also waxes of synthetic origin, for instance polyethylene waxes derived from the polymerization of ethylene, waxes obtained by Fischer-Tropsch synthesis, with a melting point >50° C., fatty acid esters and glycerides that are solid at 50° C., and silicone waxes, for instance alkyl- and alkoxy-poly(di)methylsiloxanes and/or poly(di)methylsiloxane esters that are solid at 50° C.

Advantageously, the composition of the invention contains little or no "matting" fillers and in particular less than 5% of matting filler. This is especially the case when it is desired to obtain a glossy coating on keratin materials such as the lips, the eyelashes and the hair. In contrast, fillers of this type may be used for a foundation. A matting filler is generally a filler that absorbs the skin's sweat and/or sebum, for instance silicas, talcs, clays, kaolins and polyamide powders (Nylon®).

The composition according to the invention may be manufactured by the known processes generally used in cosmetology.

The invention further provides a cosmetic process for caring for, making up or treating human keratin materials and especially human skin, facial lips and epidermal derivatives, comprising the application of the composition, especially the cosmetic composition as defined above, to the keratin materials.

The invention further provides for the use of a volatile oil in a makeup composition comprising a) at least one liquid fatty phase structured with at least one semi-crystalline polymer having an organic structure, the melting temperature of which is greater than or equal to 30° C., and b) a colorant, the liquid fatty phase, the colorant, the volatile oil and the polymer forming a physiologically acceptable medium.

The invention further provides for the use of a sufficient amount of a volatile oil in a cosmetic composition containing a physiologically acceptable medium comprising a) at least one liquid fatty phase structured with at least one semi-crystalline polymer having an organic structure, the melting temperature of which is greater than or equal to 30° C., and b) a colorant, as an agent for non-transfer of the said composition, the said composition laying down a comfortable, glossy film on keratin materials, and especially the lips.

The invention further provides for the use of a volatile oil in a makeup composition containing a physiologically acceptable medium comprising at least one liquid fatty phase structured with at least one semi-crystalline polymer having an organic structure to obtain a non-transfer cosmetic composition.

The invention is illustrated in greater detail in the examples that follow. The amounts are given as percentages by mass.

I) EXAMPLES OF MANUFACTURE OF SEMI-CRYSTALLINE POLYMERS

Example 1

Homopolymer with a Melting Point of 48° C.

120 g of Parleam are introduced into a 1 l reactor equipped with a central paddle stirrer, a condenser and a thermometer, and are heated from ambient temperature to 80° C. over 45 minutes. At 80° C., the mixture $C_1$ below is introduced over 2 hours: 40 g of cyclohexane+4 g of Trigonox 141 [2,5-bis(2-ethylhexanoylperoxy)-2,5-dimethylhexane].

30 minutes after the start of addition of the mixture $C_1$, the mixture $C_2$ is introduced over 1 hour 30 minutes, this mixture consisting of: 200 g of stearyl acrylate +400 g of cyclohexane.

At the end of the two additions, the mixture is stirred for a further 3 hours at 80° C. and all of the cyclohexane present in the reaction medium is then distilled off at atmospheric pressure. This gives the polymer at a concentration of 60% by weight of active substance in the Parleam.

Its weight-average molecular mass is of the order of 20,000-30,000 and its melting temperature $T_m$ is 48° C., measured by DSC.

Example 2

Copolymer with a Melting Point of 48° C.

The same procedure as in Example 1 is applied, except that a mixture of 10 g of N-vinylpyrrolidone and 190 g of stearyl acrylate is used.

The polymer obtained is at a concentration of 60% by weight of active substance in Parleam, its weight-average molecular mass is 43,000-53,000 and its $T_m$ is 48° C.

Example 3

Homopolymer with a Melting Point of 58° C.

The same procedure as in Example 1 is applied, except that behenyl acrylate is used instead of stearyl acrylate. The polymer obtained is at a concentration of 60% by weight of active substance in Parleam. Its weight-average molecular mass is 17,000-27,000 and its $T_m$ is 58° C.

Example 4

Copolymer with a Melting Point of 58° C.

The same procedure as in Example 2 is applied, except that behenyl acrylate is used instead of stearyl acrylate. The polymer obtained is at a concentration of 60% by weight of active substance in Parleam®. Its weight-average molecular mass is 23,500-33,500 and its $T_m$ is 58° C.

II) COMPOSITION EXAMPLES

Example 5

| | |
|---|---|
| Polymer of Example 1 | 14% |
| Polymer of Example 3 | 10% |
| Pigments | 8.7% |
| Hydrogenated isoparaffin | 16.2% |
| Solsperse 21000 | 2% |
| Isododecane | 30% |
| Phenyl silicone | 16.2% |
| Liquid lanolin | 3% |

Method of Production

Weigh out into a pan the semi-crystalline polymers and the pastes.
Incorporate the non-volatile oils and the filler.
Heat the pan on an oil bath at 100° C. (small pan) or 125° C. (large pan) with magnetic stirring.
Melt the mixture. When it is fluid and homogeneous, add the pigment millbase.
Carry out magnetic stirring for 40 minutes.
Lower the temperature to 80° C. When that temperature has been reached, add the volatile solvents.
Allow the mixture to homogenize.
Pour into the mould.

This formula was evaluated by women and ranked in relation to a prior art composition sold under the brand name Rouge Captif®. The two formulas tested are produced in the same shade. The results of the evaluation demonstrate the better gloss properties on application and after 1 h of the formula of the invention which comprises the semi-crystalline polymers. This gloss is combined with a non-transfer effect which is markedly to the benefit of the formula based on semi-crystalline polymers.

The invention claimed is:
1. A makeup composition comprising:
at least one liquid fatty phase structured with a mixture of at least one semi-crystalline polymer having an organic structure selected from low-melting polymers having a melting temperature of less than 50° C., and at least one semi-crystalline polymer having an organic structure selected from high-melting polymers having a melting temperature of at least 50° C., wherein the semi-crystalline polymers are side chain crystallizable polymers; and
wherein the ratio by weight of the low-melting point polymer to the high-melting polymer ranges from 50/50 to 90/10; and further wherein the total amount of the polymer mixture in the composition ranges from 15% to 80% by weight, relative to the total weight of the composition;
at least one colorant; and
at least one volatile oil;
wherein the liquid fatty phase, colorant, volatile oil, and polymer together form a physiologically acceptable medium.
2. The makeup composition of claim 1, wherein the at least one volatile oil has at least one of the following properties: a boiling temperature at atmospheric pressure of less than 220 C.; a vapor pressure, measured at ambient temperature and atmospheric pressure, ranging from 0.266 Pa to 40,000 Pa; and a flash point ranging from 40° C. to 100° C.
3. The makeup composition of claim 1, wherein the at least one volatile oil is chosen from
linear or cyclic silicone oils having a viscosity at ambient temperature of less than 8 cSt and optionally comprising $C_{1-10}$ alkyl or $C_{1-10}$ alkoxy groups,
volatile hydrocarbon-based oils having from 8 to 16 carbon atoms, and mixtures thereof.
4. The makeup composition of claim 3, wherein the linear or cyclic silicone oils comprise from 2 to 7 silicone atoms.

5. The makeup composition of claim 3 wherein the linear or cyclic silicon oils are chosen from octamethylcyclotetrasiloxane, decamethyl-cyclopenta-siloxane, dodecamethyl-cyclohexasiloxane, heptamethyl-hexyltrisiloxane, heptamethyl-octyl-trisiloxane, hexa-methyl-disiloxane, octamethyl-trisiloxane, decamethyl- tetrasiloxane, dodecamethyl-pentasiloxane, and mixtures thereof.

6. The makeup composition of claim 3, wherein the volatile hydrocarbon based oil is chosen from branched $C_8$-$C_{16}$ alkanes, branched $C_8$-$C_{16}$ esters, and mixtures thereof.

7. The makeup composition of claim 6, wherein the $C_8$-$C_{16}$ alkanes are chosen from $C_8$-$C_{16}$ isoalkanes.

8. The makeup composition of claim 7, wherein the $C_8$-$C_{16}$ isoalkanes are chosen from isododecane, isodecane, and isohexadecane.

9. The makeup composition of claim 6, wherein the branched $C_8$-$C_{16}$ ester is isohexyl neopentanoate.

10. The makeup composition according to claim 1, wherein the at least one volatile oil is present in an amount ranging from 20% to 50% by weight, relative to the total weight of the composition.

11. The makeup composition according to claim 10, wherein the at least one volatile oil is present in an amount ranging from 30% to 40% by weight, relative to the total weight of the composition.

12. The makeup composition according to claim 1, wherein the at least one volatile oil is present in an amount ranging from 40% to 60% by weight of the liquid fatty phase.

13. The makeup composition according to claim 12, wherein the at least one volatile oil is present in an amount ranging from 45% to 55% by weight of the liquid fatty phase.

14. The makeup composition of claim 1, wherein the weight ratio of the at least one volatile oil relative to the semi-crystalline polymers in the mixture ranges from 1 to 2.5.

15. The makeup composition of claim 14, wherein the weight ratio of the at least one volatile oil relative to the semi-crystalline polymers in the mixture ranges from 1.5 to 2.

16. The makeup composition of claim 1, wherein the semi-crystalline polymers in the mixture have a weight-average molecular mass ranging from 5,000 to 1,000,000.

17. The makeup composition of claim 16, wherein the semi-crystalline polymers in the mixture have a weight-average molecular mass ranging from 15,000 to 500,000.

18. The makeup composition of claim 1, wherein the semi-crystalline polymers in the mixture are soluble in the liquid fatty phase at a temperature greater than their melting temperature.

19. The makeup composition of claim 1, wherein the at least one semi-crystalline polymer is chosen from
- block copolymers of polyolefins of controlled crystallization,
- aliphatic or aromatic volatile polycondensates and aliphatic/aromatic covolatiles,
- homopolymers or copolymers bearing at least one crystallizable side chain, and mixtures thereof.

20. The makeup composition of claim 1, wherein the at least one semi-crystalline polymer is chosen from homopolymers and copolymers comprising from 50% to 100% by weight of units resulting from the polymerization of at least one monomer bearing at least one crystallizable hydrophobic side chain.

21. The makeup composition of claim 1, wherein the at least one semi-crystalline polymer is chosen from homopolymers and copolymers resulting from the polymerization of at least one monomer comprising at least one crystallizable side chain, of formula X:

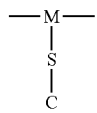

wherein M represents an atom of the polymer skeleton;
S represents a spacer;
C represents a crystallizable group, and mixtures thereof;
and S-C represents an optionally fluorinated and perfluorinated alkyl chain having at least 11 carbon atoms.

22. The makeup composition of claim 1, wherein the at least one semi-crystalline polymer is chosen from polymers resulting from the polymerization of at least one monomer chosen from acrylic acid, methacrylic acid, crotonic acid, itaconic acid, maleic acid, maleic anhydride and mixtures thereof.

23. The makeup composition of claim 1, wherein the at least one semi-crystalline polymer is chosen from homopolymers and copolymers resulting from the polymerization of at least one monomer having a crystallizable side chain.

24. The makeup composition of claim 23, wherein the at least one monomer having a crystallizable side chain is chosen from $C_{14}$ to $C_{24}$ saturated alkyl (meth)acrylates, $C_{11}$-$C_{15}$ perfluoralkyl (meth)acrylates, $C_{14}$ to $C_{24}$ N-alkyl(meth)acrylamides optionally containing a fluorine atom, vinyl esters containing $C_{14}$ to $C_{24}$ alkyl or perfluoroalkyl chains, vinyl ethers containing $C_{14}$ to $C_{24}$ alkyl or perfluoroalkyl chains, $C_{14}$ to $C_{24}$ alpha-olefins, para-alkylstyrenes with an alkyl group containing from 12 to 24 carbon atoms, and mixtures thereof.

25. The makeup composition of claim 1, wherein the at least one semi-crystalline polymers are homopolymers of alkyl (meth)acrylate or of alkyl(meth)acrylamide with a $C_{14}$ to $C_{24}$ alkyl group and/or copolymers of these monomers with a hydrophilic monomer.

26. The makeup composition of claim 1, wherein the at least one semi-crystalline polymers are copolymers of alkyl (meth)acrylate or of an alkyl(meth)acrylamide with a $C_{14}$ to $C_{24}$ alkyl group, with a monomer different in nature from (meth)acrylic acid.

27. The makeup composition of claim 26, wherein the monomer different in nature from (meth)acrylic acid is chosen from N-vinylpyrrolidone, hydroxyethyl (meth)acrylate, and mixtures thereof.

28. The makeup composition of claim 1, wherein the total amount of semi-crystalline polymers in the composition ranges from 15% to 25% by weight, relative to the total weight of the composition.

29. The makeup composition of claim 1, wherein the high-melting polymers have a melting temperature $mp_1$ ranging from 55° C. to 150° C.

30. The makeup composition of claim 29, wherein the high-melting polymers have a melting temperature $mp_1$ ranging from 60° C. to 130° C.

31. The makeup composition of claim 1, wherein the low-melting polymers have a melting temperature $mp_2$ ranging from 30° C. to less than 50° C.

32. The makeup composition of claim 31, wherein the ratio by weight of the at least one semi-crystalline polymer selected from low-melting polymers to the at least one semi-crystalline polymer selected from high-melting polymers is 50/50.

33. The makeup composition of claim 1, wherein the at least one liquid fatty phase comprises at least one polar oil and isononyl isononanoate.

34. The makeup composition of claim 1, wherein the weight ratio of the semi-crystalline polymers in the mixture to the at least one liquid fatty phase ranges from 0.20 to 0.60.

35. The makeup composition of claim 34, wherein the weight ratio of the semi-crystalline polymers in the mixture to the at least one liquid fatty phase ranges from 0.25 to 0.50.

36. The makeup composition of claim 1, wherein the composition contains less than 10% by weight of wax and/or less than 5% by weight of matting filler, relative to the total weight of the composition.

37. The makeup composition of claim 1, wherein the composition is in anhydrous form.

38. The makeup composition of claim 1, wherein the composition is in cast form.

39. The makeup composition of claim 1, wherein the composition is in the form of a mascara, eyeliner, foundation, lipstick, deodorant, body makeup product, eyeshadow, rouge, or concealer product.

40. The makeup composition of claim 39, wherein the makeup composition is in the form of a solid stick with a hardness ranging from 100 to 350 gf.

41. A lipstick comprising:
at least one liquid fatty phase structured with at least one semi-crystalline polymer having an organic structure and the melting temperature $mp_1$ of which ranges from 55° C. to 150° C., and at least one semi-crystalline polymer having an organic structure and the melting temperature $mp_2$ of which ranges from 30° C. to 50° C., wherein the semi-crystalline polymers are side chain crystallizable polymers; and
wherein the ratio by weight of the low-melting point polymer to the high-melting polymer ranges from 50/50 to 90/10; and further wherein the total amount of the polymer mixture in the composition ranges from 15% to 80% by weight, relative to the total weight of the composition;
at least one colorant; and
at least one volatile oil.

42. A cosmetic makeup process comprising applying to a keratin material a makeup composition comprising:
at least one liquid fatty phase structured with a mixture of at least one semi-crystalline polymer having an organic structure selected from low-melting polymers having a melting temperature of less than 50° C., and at least one semi-crystalline polymer having an organic structure selected from high-melting polymers having a melting temperature of at least 50° C., wherein the semi-crystalline polymers are side chain crystallizable polymers; and
wherein the ratio by weight of the low-melting point polymer to the high-melting polymer ranges from 50/50 to 90/10; and further wherein the total amount of the polymer mixture in the composition ranges from 15% to 80% by weight, relative to the total weight of the composition;
at least one colorant; and
at least one volatile oil;
wherein the liquid fatty phase, colorant, volatile oil and polymer together form a physiologically acceptable medium.

43. The cosmetic makeup process of claim 42, wherein at least one of the semi-crystalline polymers in the mixture has a melting temperature greater than the temperature of the keratin material.

44. The cosmetic makeup composition of claim 43, wherein the keratin material is the skin or the lips.

45. A process for obtaining a glossy composition, said process comprising
including at least one volatile oil in a makeup composition comprising a physiologically acceptable medium comprising:
at least one liquid fatty phase structured with a mixture of at least one semi-crystalline polymer having an organic structure selected from low-melting polymers having a melting temperature of less than 50° C., and at least one semi-crystalline polymer having an organic structure selected from high-melting polymers having a melting temperature of at least 50° C., wherein the semi-crystalline polymers are side chain crystallizable polymers; and
wherein the ratio by weight of the low-melting point polymer to the high-melting polymer ranges from 50/50 to 90/10; and further wherein the total amount of the polymer mixture in the composition ranges from 15% to 80% by weight, relative to the total weight of the composition; and
at least one colorant, and
applying said composition to a keratin material whereby a non-transfer film is formed.

46. The cosmetic makeup process of claim 45, wherein the keratin material is the lips.

47. A process for obtaining a non-transfer composition that forms a glossy and comfortable coating when applied to a substrate, said process comprising including at least one volatile oil in a makeup composition comprising a physiologically acceptable medium comprising at least one liquid fatty phase structured with a mixture of at least one semi-crystalline polymer having an organic structure selected from low-melting polymers having a melting temperature of less than 50° C., and at least one semi-crystalline polymer having an organic structure selected from high-melting polymers having a melting temperature of at least 50° C., wherein the semi-crystalline polymers are side chain crystallizable polymers; and
wherein the ratio by weight of the low-melting point polymer to the high-melting polymer ranges from 50/50 to 90/10; and further wherein the total amount of the polymer mixture in the composition ranges from 15% to 80% by weight, relative to the total weight of the composition.

* * * * *